US012740895B2

(12) United States Patent
Tollini et al.

(10) Patent No.: US 12,740,895 B2
(45) Date of Patent: Sep. 22, 2026

(54) MOBILE WOUND COVER

(71) Applicants: Dennis R. Tollini, Clarence Center, NY (US); Michael D. Tollini, Clarence Center, NY (US); Randel B. Holmes, Knoxville, TN (US); Gary Kaufman, Williamsville, NY (US); Thomas P Stewart, Orchard Park, NY (US)

(72) Inventors: Dennis R. Tollini, Clarence Center, NY (US); Michael D. Tollini, Clarence Center, NY (US); Randel B. Holmes, Knoxville, TN (US); Gary Kaufman, Williamsville, NY (US); Thomas P Stewart, Orchard Park, NY (US)

( * ) Notice: Subject to any disclaimer, the term of this patent is extended or adjusted under 35 U.S.C. 154(b) by 0 days.

(21) Appl. No.: 18/647,839

(22) Filed: Apr. 26, 2024

(65) Prior Publication Data

US 2024/0358552 A1 Oct. 31, 2024

Related U.S. Application Data

(60) Provisional application No. 63/498,885, filed on Apr. 28, 2023.

(51) Int. Cl.

| | |
|---|---|
| ***A61F 13/0246*** | (2024.01) |
| ***A61F 13/02*** | (2024.01) |
| ***A61F 13/0206*** | (2024.01) |

(52) U.S. Cl.

CPC ........ *A61F 13/025* (2013.01); *A61F 13/0206* (2013.01); *A61F 13/0253* (2013.01); *A61F 13/0266* (2013.01)

(58) Field of Classification Search

CPC .. A61F 15/008; A61F 13/00; A61F 13/00008; A61F 13/00021; A61F 13/02; A61F 13/025; A61F 13/0206; A61F 13/0253; A61F 13/0266; A61F 13/0246; A61F 2013/00089; A61J 13/00

USPC .......... 602/41, 42, 46, 54, 58; 128/887, 888, 128/889, 890

See application file for complete search history.

(56) References Cited

U.S. PATENT DOCUMENTS

| | | | |
|---|---|---|---|
| 5,060,662 | A | 10/1991 | Farnswoth, III |
| 6,143,945 | A | 11/2000 | Augustine et al. |
| 6,320,093 | B1 | 11/2001 | Augustine et al. |
| 6,420,623 | B2 | 7/2002 | Augustine et al. |
| 6,570,050 | B2 | 5/2003 | Augustine et al. |
| 7,576,257 | B2 | 8/2009 | Lagreca, Sr. |
| 8,722,960 | B2 | 5/2014 | Aali et al. |
| 9,717,828 | B2 | 8/2017 | Hartmann |

*Primary Examiner* — Caitlin A Carreiro

(74) *Attorney, Agent, or Firm* — Simpson & Simpson, PLLC

(57) ABSTRACT

A mobile wound cover including a skin adhesion rim having a skin adhesion layer and an oppositely disposed rim adhesion layer, the skin adhesion rim having a first aperture therein a protective rim having a skin surface and a cover surface, the skin surface arranged to secure to the skin adhesion layer of the skin adhesion rim, the protective rim having a second aperture therein, and a cover, the cover arranged to removably engage the cover surface of the protective rim, the cover further including a removable securement means arranged to removably secure the cover to the cover surface of the protective rim, the securement means disposed a distal surface of the cover, the cover being at least semi-transparent.

14 Claims, 5 Drawing Sheets

10
100
206
106
320
110
322
324
214
200
112
W
114
S

MOBILE WOUND COVER

CROSS-REFERENCE TO RELATED APPLICATIONS

This application claims priority pursuant to 35 U.S.C. 119(e) to U.S. Provisional Patent Application No. 63/498,885, filed Apr. 28, 2023, which application is incorporated by reference in its entirety herein.

FIELD

The present invention relates to a wound cover, particularly a mobile wound cover that provides variable moisture vapor transmission rates (MVTR) to a wound theater and is arranged to provide continuous access to the wound theater.

BACKGROUND

Typically, wounds are visible from the epidermis (outer skin layer) of a patient. These wounds can penetrate the dermis (the middle layer containing blood vessels, nerve endings, etc.) and in other cases, the wounds can penetrate further into the hypodermis, or subcutaneous tissue, (the deepest skin later composed of connective and adipose tissue containing major blood vessels, nerves, and lymphatic vessels). Regardless of the depth of the wound in the tissue, healing of wounds that penetrate the dermis, hypodermis, and beyond, require specialized wound treatment to heal efficiently and properly.

As wounds begin to heal, there is a specific sequence of molecular and cellular events. Within the first day, or less, blood clotting occurs and this is followed by a vascular response, typically around day three post-injury—this is known as the first stage of wound healing, i.e., hemostasis. Beginning within the first day of injury, inflammation occurs, usually lasting several days. Inflammation is usually defined by the presence of two inflammatory cells, neutrophils and macrophages, which kill bacteria and provide biological regulators (growth factors, cytokines and bioactive lipid products) to advance the healing process. Around five to seven days after the initial injury and during the inflammation period, the proliferation phase begins, which is generally defined by the formation of a new matrix of cells (fibrin, fibronectin, collagens, proteoglycans, glycosaminoglycans (GAGs), and other glycoproteins). The proliferation period uses the new matrix of cells to contract the wound edges, i.e., bring them closer to close the wound. Finally, at about 14 to 21 days post-injury, the maturation phase begins (within three weeks of injury, the skin is restored to approximately 20% tensile strength) and continues up to a year later-restoring the new skin to 70% to 80% tensile strength. The maturation phase is also when scarring occurs (an avascular, acellular mass of collagen).

An essential component to the advanced biological process of wound healing is the prevention of biofilm formation-bacteria forming a protective community before they can be killed by the immune system, antibiotics, or debridement (removal of infected, dead, damaged tissue from a wound).

As such, wound covers assist in the prevention of biofilm formation by isolating the wound theater (wound location) from excessive exposure to bacteria. However, covering a wound in a manner that disrupts adequate oxygen supply to the wound will delay the healing process. For a wound to heal, it must have a microenvironment free from the non-viable tissue that serves as a bacterial culture medium to increase organism proliferation. Oxygen is a primary requirement for this energy-dependent metabolic process to occur. The production of free radicals kills bacteria, facilitating the proliferation of fibroblasts and epithelial cells, which are crucial for efficient and expediated wound healing, thus the need for sufficient oxygen exchange with the wound theater, in addition to moisture vapor transmission, e.g., moisture vapor transmission rate (MVTR).

Thus, there is a long felt need for a wound cover that protects a wound theater such that excess bacteria cannot build up, allows for adequate oxygen supply to the wound, and also provides for interruptibility (i.e., access) to allow for wound debridement and/or visualization and application of additional treatment modalities to the wound. In other words, there is a need for a wound cover or dressing that covers the wound while also providing moisture vapor transmission therethrough.

There is also a long felt need for a wound cover that includes a removable cover which is positioned at a distance from a surface of the wound to prevent accidental impact to the wound.

SUMMARY

According to aspects illustrated herein, the present invention generally relates to a wound cover, or bandage-like, or wound dressing-like, device. Particularly, the design of the invention provides a lid, or top cover, which releasably secures to an outer body, or rim, allowing access to a wound, or wound theater, substantially contained within the rim.

In one possible configuration, the wound cover or mobile wound cover may comprise a skin adhesion rim having a skin adhesion layer and an oppositely disposed rim adhesion layer, the skin adhesion rim having a first aperture therein a protective rim having a skin surface and a cover surface, the skin surface arranged to secure to the skin adhesion layer of the skin adhesion rim, the protective rim having a second aperture therein, and a cover, the cover arranged to removably engage the cover surface of the protective rim, the cover further including a removable securement means arranged to removably secure the cover to the cover surface of the protective rim, the securement means disposed a distal surface of the cover, the cover being at least semi-transparent.

In some embodiments, the protective rim of the aforementioned wound cover may be comprised of a hydrophilic material, wherein the protective rim is arranged to create a vertical distance between a distal surface of the skin adhesion rim and the cover.

In other arrangements, the securement means of the aforementioned wound cover may comprise a single-sided adhesive secured to the cover surface of the rim, the single-sided adhesive comprising an adhesive surface adhered to the cover surface of the rim and an oppositely disposed blocker surface, and a double-sided adhesive secured to the distal surface of the cover, the cover comprising a transparent film, wherein the double-sided adhesive is adapted to releasably adhere to the blocker surface of the single-sided adhesive.

In further configurations, the aforementioned double-sided adhesive may be arranged proximate an external edge of the cover thereby forming a non-adhesive section on the distal surface of the cover, where the non-adhesive section defines the window of the mobile wound cover.

In other embodiments, the protective rim may be comprised of a foam and the foam may be hydrophilic.

In an exemplary arrangement, the skin adhesion rim of the aforementioned mobile wound cover may comprise a double-sided adhesive, the skin adhesion layer comprising a first adhesive and the rim adhesion layer comprising a second adhesive, the first and second adhesives arranged on opposite sides of a carrier layer disposed therebetween.

Therefore it is a general object of the present invention to provide a mobile wound dressing, wound cover, wound bandage, which has a cover arranged on a protective rim surrounding a wound, which cover includes a transparent portion to allow viewing of the wound without removal thereof and where the cover releasably secures to the protective rim allowing access to the wound and re-closure of the cover-thus eliminating the need to redress the wound.

These and other objects, features, and advantages of the present invention will become readily apparent upon a review of the following detailed description of the invention, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which.

Figures 1, 1A, 1B:
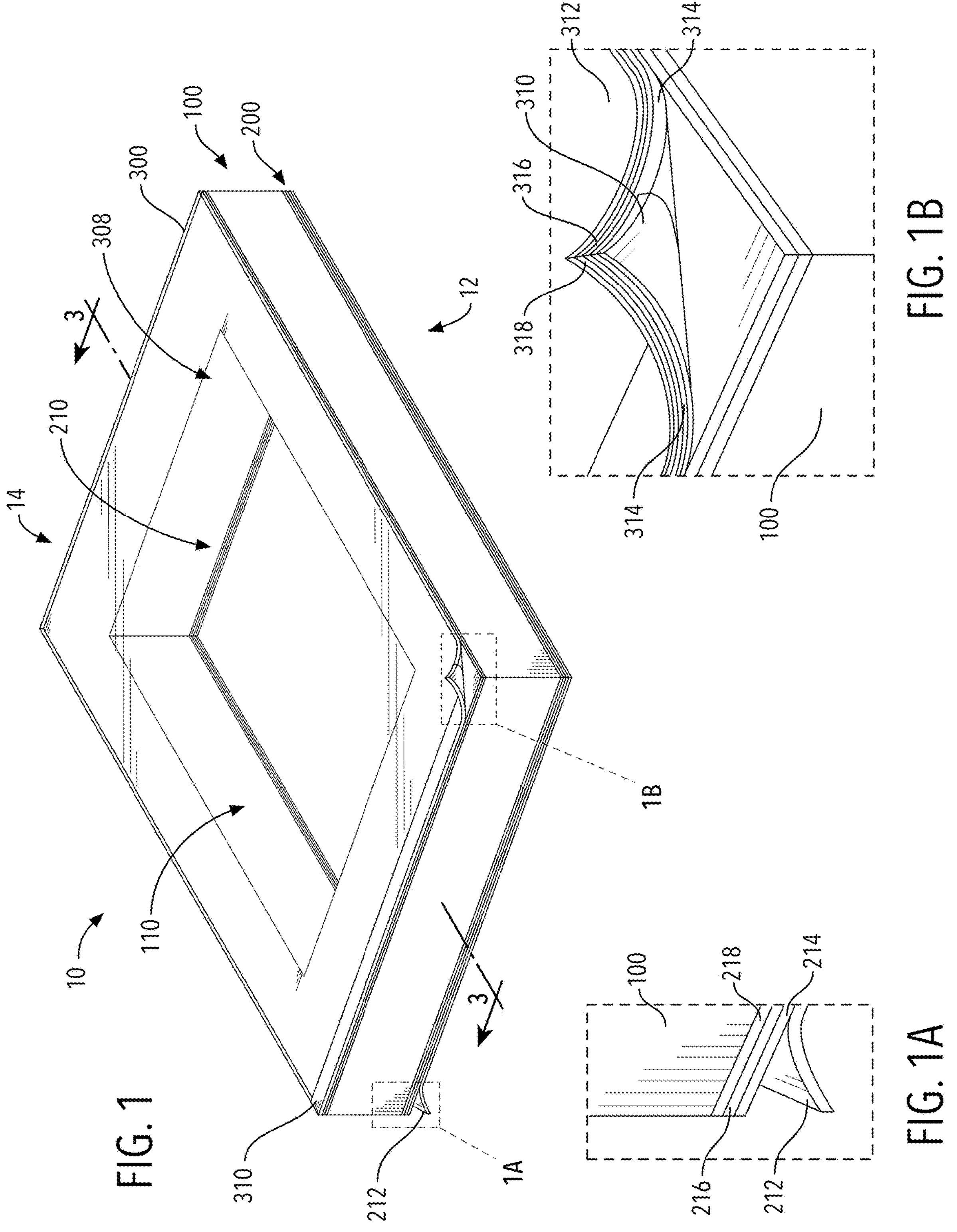
FIG. 1 is a perspective view of the present invention.
FIG. 1A is an enlarged view taken generally from 1A in FIG. 1.
FIG. 1B is an enlarged view taken generally from 1B in FIG. 1.

It should be appreciated that the drawings are for exemplary purposes only and are not drawn to scale. In the present drawings, actual proportional dimensions are exaggerated to illustrate the components of the present invention and the appending claims are not restricted to any specific dimension or proportion.

DETAILED DESCRIPTION

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

It should be understood that use of "or" in the present application is with respect to a "non-exclusive" arrangement, unless stated otherwise. For example, when saying that "item x is A or B," it is understood that this can mean one of the following: (1) item x is only one or the other of A and B; (2) item x is both A and B. Alternately stated, the word "or" is not used to define an "exclusive or" arrangement. For example, an "exclusive or" arrangement for the statement "item x is A or B" would require that x can be only one of A and B. Furthermore, as used herein, "and/or" is intended to mean a grammatical conjunction used to indicate that one or more of the elements or conditions recited may be included or occur. For example, a device comprising a first element, a second element and/or a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element.

Moreover, as used herein, the phrases "comprises at least one of" and "comprising at least one of" in combination with a system or element is intended to mean that the system or element includes one or more of the elements listed after the phrase. For example, a device comprising at least one of: a first element; a second element; and, a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element. A similar interpretation is intended when the phrase "used in at least one of:" is used herein.

It should be noted that the terms "distal" and "proximal" are intended to be directional terms, e.g., a proximal component meaning "above" a distal component.

It should be appreciated that the term "interruptibility" or "access" is intended to mean that an object and/or structure may exist in an open or closed configuration, that is, an exposed configuration or a sealed configuration. In other words, a wound cover having an interruptible configuration means that a wound covered by the wound cover may be substantially isolated from an outside environment (inaccessible when a cover is engaged) or exposed to the outside environment (accessible when the cover is at least partially disengaged).

It should be noted that, in various illustrations, leader lines may be terminated with a solid dot which should be interpreted to mean that the indicated component may also include the described structural element and/or elements.

FIGS. 1, 1A, and 1B generally illustrate a perspective view of a representative mobile wound cover and a pair of enlarged views, respectively. In one possible configuration, mobile wound cover 10 generally includes skin adhesion rim 200, protective rim 100, and cover 300. Skin adhesion rim 200 may comprise adhesion layer 214, carrier layer 216, and adhesive layer 218, where adhesive layers 214 and 218 are fixedly secured on opposite faces of carrier layer 216, thereby exposing adhesive elements thereon. Skin adhesion layer 200 includes aperture 210 therein. Protective rim 100 may additionally include adhesive layer 112 fixedly secured to a top or proximal surface thereof, which adhesive layer 112 has backing 114, e.g., non-adhesive backing, disposed on an opposite surface thereof. Protective rim 100 includes aperture 110 therein. Cover 300 may comprise adhesive layer 314, carrier layer 316, adhesive layer 318, and film 312, where adhesive layers 314 and 318 are fixedly secured on opposite faces of carrier layer 316 and adhesive layer 318 is fixedly secured to a bottom or distal face of film 312. In some embodiments, mobile wound cover 10 may also include blocker 212 releasably affixed to adhesive layer 214 of skin adhesion rim. In other configurations, mobile wound cover 10 may also include blocker 310 fixedly secured to adhesive layer 314 of cover 300 and arranged proximate an external edge thereof, as generally shown in FIGS. 1 and 1B.

As shown in FIG. 1A, blocker 212 is releasably secured to adhesive layer 214, thereby blocking the adhesive element of adhesive layer 214 and is adapted to keep the adhesive element free from debris until blocker 212 is removed and adhesive layer 214 is applied to a patient, i.e., the skin.

As shown in FIG. 1B, blocker 310 is fixedly secured to a portion of adhesive layer 314 proximate an external edge thereof, thus, blocker 310 functions as a tab since blocker 310 freely rests on backing 114 of protective rim 100, whereas the remaining area of adhesive layer 314 releasably affixes to, i.e., sticks to, backing 114 of protective rim 100. Blocker 310 may be described as a pull-tab, which allows a medical practitioner to pull blocker 310 away from backing 114 thereby releasing or detaching adhesive layer 314 of cover 300 from backing 114 of protective rim 100 to expose apertures 110 and 210.

As generally shown, cover 300 is arranged to releasably seal aperture 110 of protective rim 100, proximate proximal surface 14, when releasably attached to backing 114 of protective rim 100. Thus, cover 300 is releasably secured, i.e., adhesively in a removable manner, to all of the surrounding surfaces of the edges of aperture 110, thus forming window 308, i.e., at least a semi-transparent section thereof, into aperture 110. Window 308 may also be defined as the portion of cover 300 that is above aperture 110 and that portion is at least partially taught, thereby providing a degree of protection over aperture 110. In some embodiments, cover 300, less blocker 310, is at least semi-transparent, preferably transparent, i.e., the entirety of cover 300 is a window.

It should be noted that in alternative embodiments of mobile wound cover 10, cover 300 may be fixedly secured to protective rim 100 at a portion thereof and oppositely disposed in relation to blocker 310 such that cover 300 cannot be completely removed.

Figures 2, 2A:
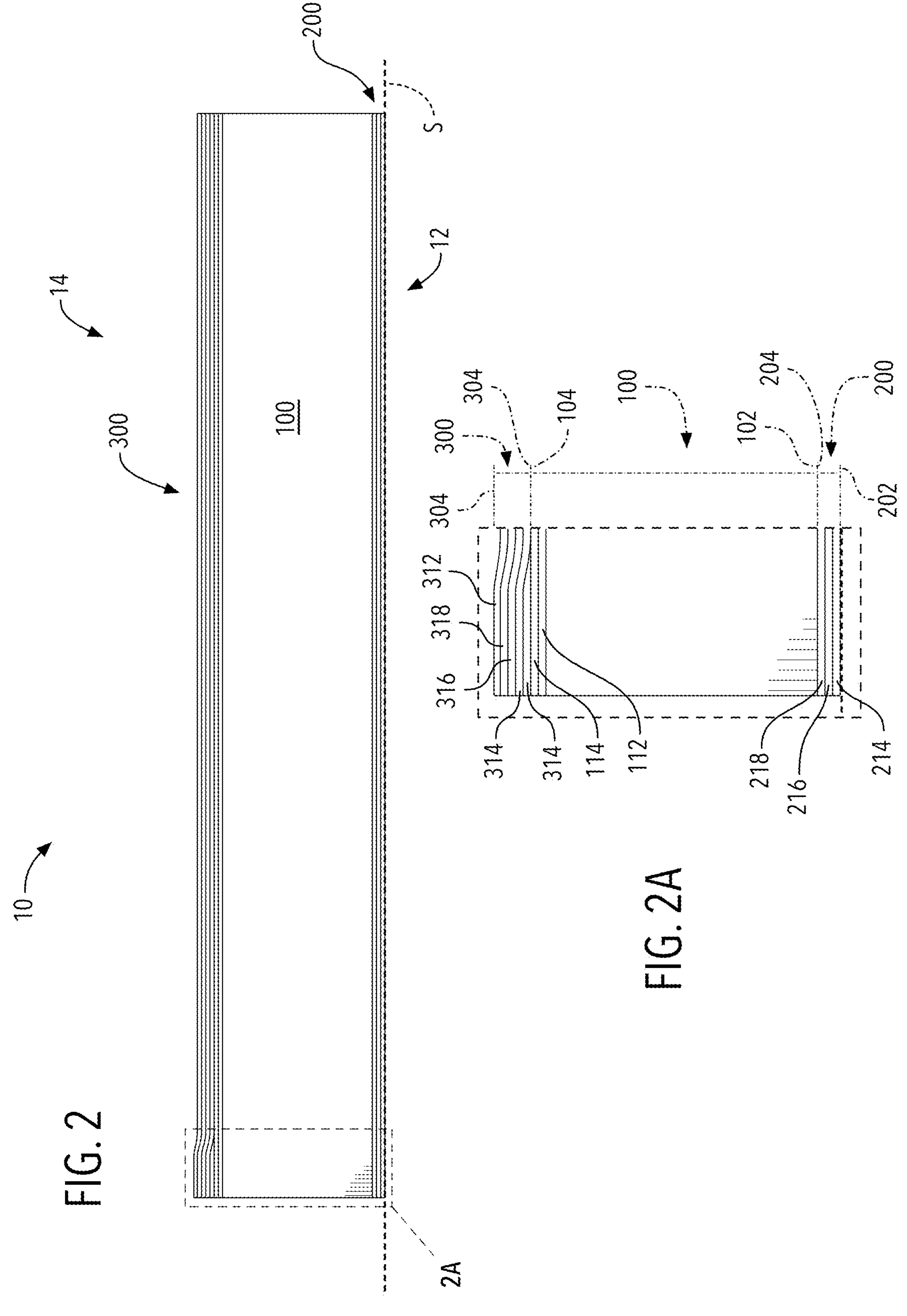
FIG. 2 is a right-side view of the invention shown in FIG. 1.
FIG. 2A is an enlarged view taken generally from 2A in FIG. 2.

In reference to FIGS. 2 and 2A, which show a right-side view and respective enlarged view of mobile wound cover 10 adhered to skin S of a patient, mobile wound cover 10 generally has distal surface 12 (e.g., blocker 212 in FIG. 1 and/or adhesive layer 214 when blocker 212 is removed) and proximal surface 14 (e.g., film 312 of cover 300). In some embodiments, protective rim 100 includes skin surface 102 and cover surface 104, specifically, skin surface 102 is arranged proximate distal surface 12 and is the surface in which adhesive layer 218 adheres to and cover surface 104 (e.g., backing 114) is arranged proximate proximal surface 14 and is the surface in which cover 300, i.e., adhesive layer 310, releasably adheres to. In some arrangements, skin adhesion rim 200 includes skin adhesion surface 202, e.g., adhesive layer 218, and rim adhesion surface 204, e.g., adhesive layer 214, wherein skin adhesion surface 202 is arranged to adhere to skin S and rim adhesion surface 204 is arranged to fixedly secure skin adhesion rim 200 to skin surface 102 of protective rim 100.

Figures 3, 3A:
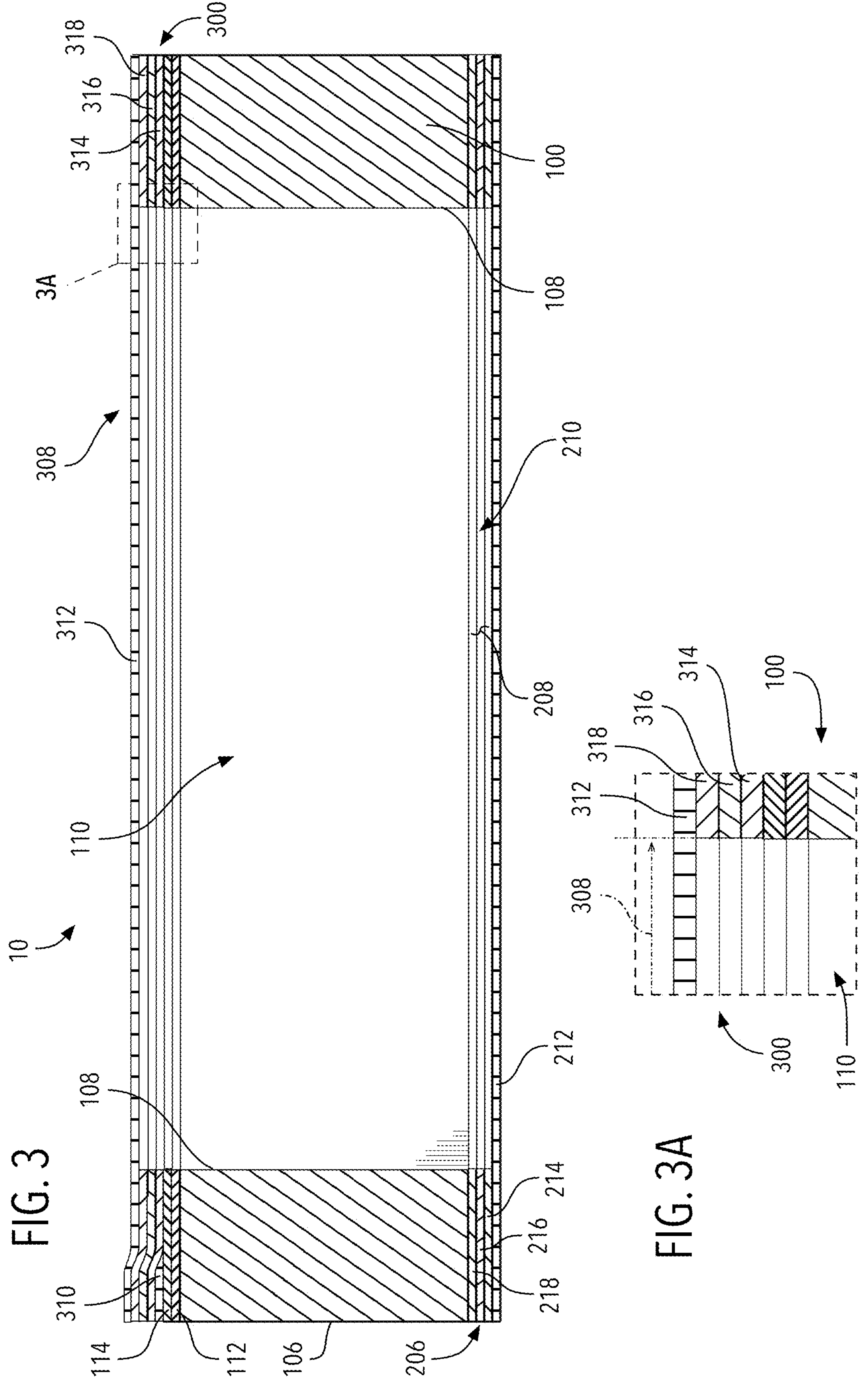
FIG. 3 is a cross-sectional view taken generally along line 3-3 in FIG. 1.
FIG. 3A is an enlarged view taken generally from 3A in FIG. 3.

FIG. 3 shows a cross-sectional view taken generally along line 3-3 in FIG. 1. As generally shown, aperture 110 is formed by a space arranged in protective rim 100 along with adhesive layer 112 and backing 114, and aperture 210 is formed by a space in adhesive layer 214, carrier layer 216, and adhesive layer 218. Similarly, adhesive layer 314, carrier layer 316, and adhesive layer 318 all have a space therein, which space is substantially colinear within inner edge 108 of protective rim 100 and inner edge 208 of skin adhesion layer 200. In can also be said that inner edge 108 is the internal wall of aperture 110 and inner edge 208 is the internal wall of aperture 210.

In reference to FIGS. 3 and 3A, FIG. 3A is an enlarged view taken generally from 3A in FIG. 3. It should be noted that window 308 may reference a portion of cover 300, specifically film 312, that is at least semi-transparent or translucent, when the entirety of film 312 is not at least semi-transparent or translucent. Further, window 308 references a portion of film 312 of cover 300 which is arranged over aperture 110 (and aperture 210) and does not have any components arranged thereunder, less blocker 212 when releasably adhered to adhesive layer 214. Window 308 is at least a portion of film 312 which is at least semi-permeable, thereby allowing moisture vapor transmission therethrough and from a wound arranged within and/or substantially contained within apertures 110 and 210 when cover 300 is releasably arranged thereover. Thus, in some embodiments, film 314 may be comprised of one or more of a semi-permeable material, semi-occlusive material, or a combination thereof, e.g., semi-permeable polyurethane film, or comparable material having the aforementioned characteristics.

Figure 4:
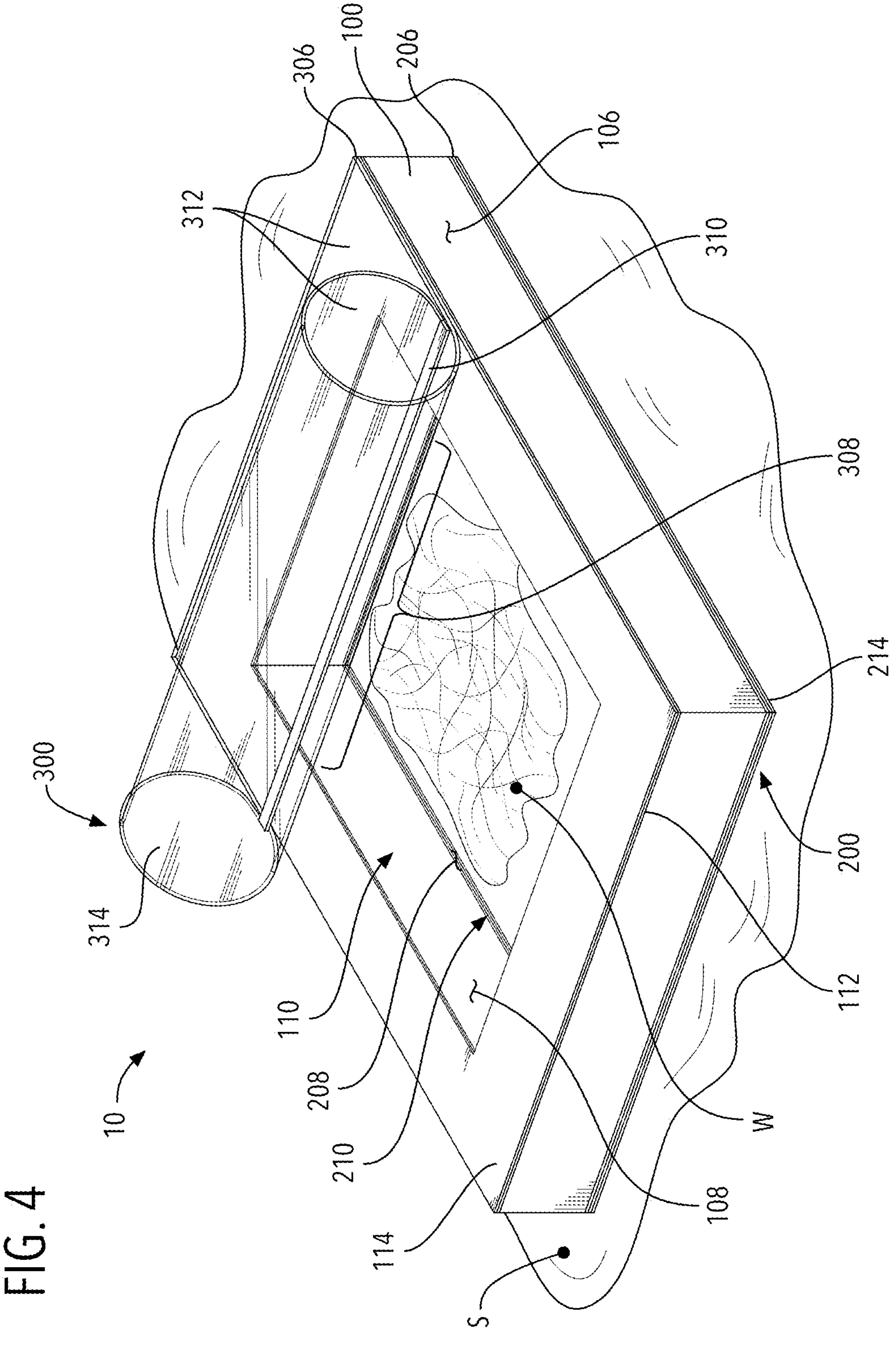
FIG. 4 is a perspective view of the invention shown in FIG. 1 with the cover partially removed; and, FIG. 5 is a perspective view of the invention shown in FIG. 1, with the cover removed, illustrating a plurality of removable portions.

In reference to the aforementioned figures and FIG. 4, FIG. 4 generally shows mobile wound cover 10 adhered to skin S of a patient and with cover 300 partially removed and exposing apertures 110 and 210 having wound W therein. As shown, protective rim 100 surrounds wound W and provides a vertical distance between the surface of wound W and the top surface of protective rim, e.g., backing 114. Cover 300 is shown partially open and releasably adhered to film 312 of cover 300 via adhesive layer 314. This allows cover 300 to remain open, opening apertures 110 and 210 to expose wound W, thereby allowing access thereto for treatment and/or debridement without having to physically keep cover 300 open. When the treatment and/or debridement is concluded, a provider can recover apertures 110 and 210 (e.g., the configuration shown in FIG. 1). Backing 114 is made of a material that allows adhesive layer 314 to releasably and repeatedly adhere thereto, allowing cover 300 to be opened and closed multiple times.

In alternative embodiments, an additional adhesive portion or section is arranged on a surface of film 312 proximate proximal surface 14 (See FIG. 1) and proximate blocker 310, thus allowing cover to be folded over and releasably adhered to film 312 so that cover 300 does not need to be completely turned over for adhesive layer 314 to be exposed to be releasably adhered to film 312.

Figure 5:
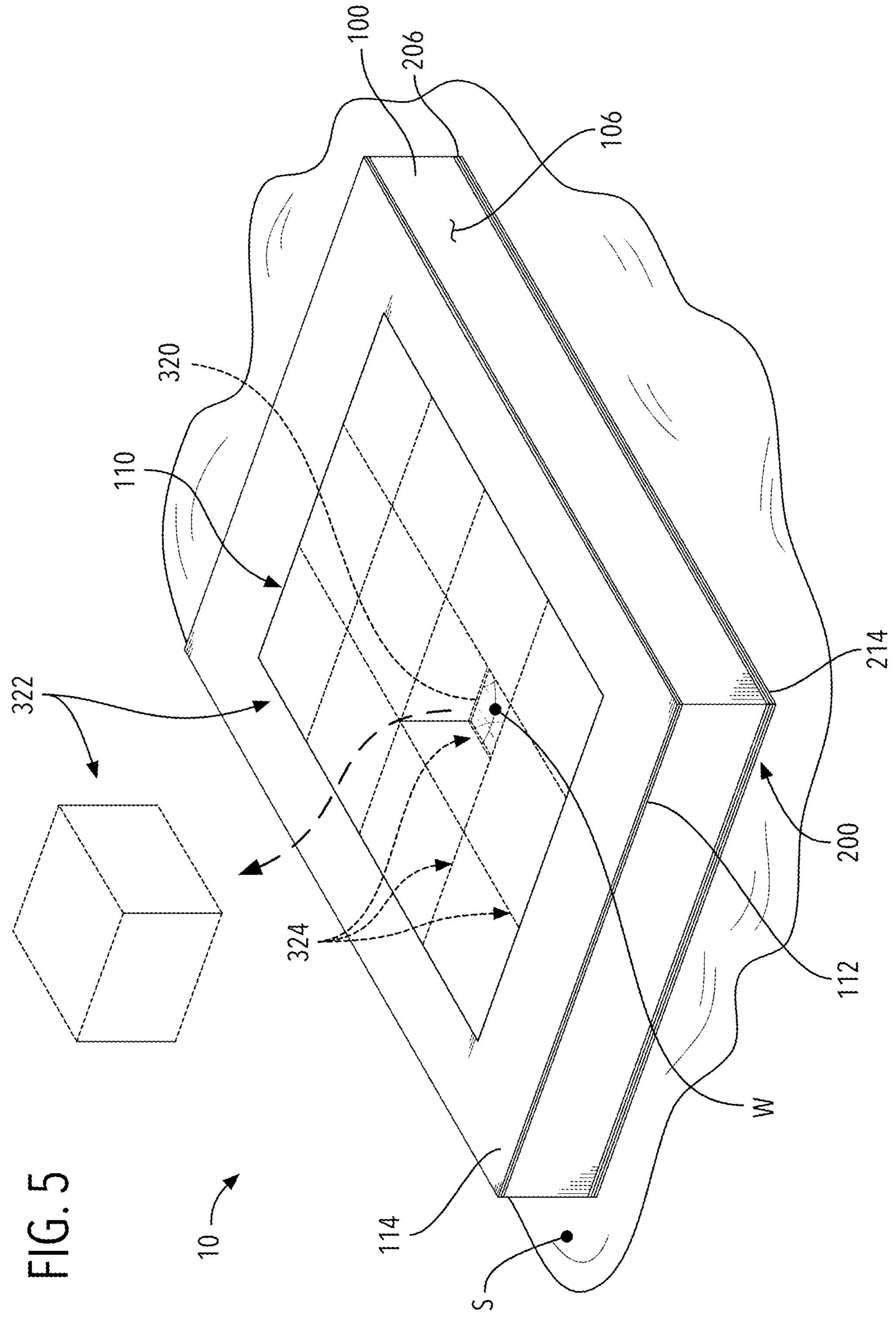

FIG. 5 illustrates a perspective view of an alternative embodiment of mobile wound cover 10, shown adhered on skin S of a patient. For clarity of illustration, the cover is not shown, but it should be appreciated that the cover is intended to be a corresponding element of this embodiment. This embodiment features perforation portion 320 arranged within aperture 110 of protective rim 100. Perforation portion 320 may be an extension of skin adhesion rim 200, or may be a separate layer disposed between skin adhesion rim 200 and protective rim 100. Perforation portion 320 is comprised of plurality of removable portions 322, which are defined, in a non-restrictive manner, by a grid of perforations 324. As depicted, individual removable portions 322 can be selectively detached and removed along the perforations 324. This allows a medical provider, or user, to customize the opening within mobile wound cover 10 to substantially conform to the size and shape of wound W, while the remaining removable portions 322 continue to cover the area surrounding the wound.

Those in the art will understand that any suitable material, now known or hereafter developed, may be used in forming the present invention described herein.

In some configurations, adhesive layer 314, carrier layer 316, and adhesive layer 318 form a double-sided adhesive attached to film 312 to form cover 300. Thus, double-sided adhesive may be 3M™ Double Coated Medical Polyethylene Film Tape, Product No. 1509. In some embodiments, adhesive layers 314 and 318 may be comprised of a tackified acrylic-based pressure sensitive adhesive, or a comparable pressure sensitive adhesive, which adhesive layers are preferably configured as being at least partially transparent. In some embodiments, carrier layer 316 may be comprised of polyethylene film, either translucent, or at least partially transparent. It should be noted that protective rim 200 may be comprised of a double-sided adhesive and have similar components as the aforementioned, e.g., adhesive layers 214 and 218 may be comprised of a tackified acrylic-based pressure sensitive adhesive, or a comparable pressure sensitive adhesive, which adhesive layers are preferably configured as being at least partially transparent, and carrier layer 216 may be comprised of polyethylene film, either translucent, or at least partially transparent.

In some embodiments, backing 114 and adhesive layer 112 of cover surface 104 of protective rim 100 may be 3M™ Single Coated Polyester Medical Tape, Product No. 1516. In some embodiments, adhesive layer 112 may be comprised of tackified acrylic-based pressure sensitive adhesive, or a comparable pressure sensitive adhesive, which adhesive layer is preferably configured as being at least partially transparent. In some embodiments, backing 114 may be comprised of a transparent film, preferably transparent polyester film, backing 114 and adhesive layer 112 are fixedly secured together to form cover surface 104.

In one possible arrangement, protective rim 100 is comprised of a hydrophilic material, preferably a hydrophilic foam.

It should be appreciated that the aforementioned rim provides for a distance between the surface of wound W and the internal surface (i.e., bottom surface) of the cover (i.e., lid)—such that compression on the cover and/or rim will not impact the surface of the wound and disrupt the healing process, and/or move potential biofilm into a location of the wound where it could potentially be absorbed.

One having ordinary skill in the art would appreciate that the various components of mobile wound cover 10 are interchangeable, thus, various combinations thereof are contemplated within the scope of the appending claims.

EXAMPLES

The following description is merely exemplary; thus, the reference numerals are for illustrative purposes only and should not be considered restrictive on the scope of the appending claims:

Example 1

A mobile wound cover (10), comprising:

a skin adhesion rim (200) having a skin adhesive surface (202) and/or skin adhesion layer (214) and an oppositely disposed rim adhesive surface (204) and/or rim adhesion layer (218), the skin adhesion rim (200) having a first aperture (210) therein;

a protective rim (100), having a skin surface (102) and a cover surface (104), the skin surface (102) arranged to secure to the skin adhesive surface (202) and/or skin adhesion layer (214) of the skin adhesion rim (200), the protective rim having a second aperture (110) therein; and, a cover (300), the cover (300) arranged to removably engage the cover surface (104) of the protective rim (100), said cover (300) further including a removable securement means (314) arranged to removably secure the cover (300) to the cover surface (104) of the protective rim (100), the securement means (314) on a distal surface of the cover (300), the cover (300) being at least semi-transparent.

It should be noted that in the aforementioned example, the removable securement means may be disposed on one or more of either the cover, or the protective rim, or both.

Example 2

A mobile wound cover (10), comprising:

a skin adhesion rim (200) comprising a double-sided adhesive (214, 216, 218) and a first aperture (210) therein;

a protective rim (100), having a skin surface (102) and a cover surface (104), said skin surface (102) fixedly secured to one side of said double-sided adhesive (218) of said skin adhesion rim (200), said protective rim (100) having a second aperture (110) therein, said cover surface (104) having a backing (114) fixedly secured (via 112) thereto; and, a cover (300), said cover arranged to removably engage said cover surface (104) of said protective rim (100), said cover (300) comprising:

a double-sided adhesive (314, 316, 318); a film (312) fixedly secured to a first side of said double-sided adhesive (318); and, a blocker (310) fixedly secured to at least a portion of a second side (314) of said double-sided adhesive (314, 316, 318), wherein said double-sided adhesive (314) of said cover (300) is adapted to releasably secure to said backing (114) of said protective rim (100), thereby removably covering a proximal opening of said second aperture (110).

It should be noted that the aforementioned backing and adhesive, e.g., backing 114 and adhesive layer 112, may alternatively arranged on the cover and the double-sided adhesive of the cover may be alternatively arranged as the cover surface of the protection rim.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMERALS

10 Mobile wound cover
12 Distal surface
14 Proximal surface
100 Protective rim
102 Skin surface
104 Cover surface
106 Outer edge
108 Inner edge
110 Aperture
112 Adhesive layer
114 Backing
200 Skin adhesion rim
202 Skin adhesion surface
204 Rim adhesion surface
206 Outer edge
208 Inner edge
210 Aperture
212 Blocker
214 Adhesive layer
216 Carrier layer
218 Adhesive layer
300 Cover
302 Distal surface
304 Proximal surface
306 Outer edge
308 Window
310 Cover blocker
312 Film
314 Adhesive layer
316 Carrier layer
318 Adhesive layer
320 Perforation portion of perforation layer
322 Removable portions
324 Perforations
S Skin
W Wound

What is claimed is:

1. A mobile wound cover, comprising:

a skin adhesion rim having a skin adhesion layer and an oppositely disposed rim adhesion layer, said skin adhesion rim having a first aperture therein, said skin adhesion rim further comprises a perforation portion having a plurality of removable sections, said perforation portion being arranged within said first aperture;

a protective rim, having a skin surface and a cover surface, said skin surface arranged to secure to said rim adhesion layer of said skin adhesion rim, said protective rim having a second aperture therein; and, a cover, said cover arranged to removably engage said cover surface of said protective rim, said cover further including a removable securement means arranged to removably secure said cover to said cover surface of said protective rim, said securement means disposed on a distal surface of said cover, said cover being at least semi-transparent, said securement means comprise:

a single-sided adhesive secured to said cover surface of said protective rim, said single-sided adhesive comprising an adhesive surface adhered to said cover surface of said protective rim and an oppositely disposed blocker surface; and, a double-sided adhesive secured to said distal surface of said cover, said cover comprising a transparent film, wherein said double-sided adhesive is adapted to releasably adhere to said blocker surface of said single-sided adhesive.

2. The mobile wound cover recited in claim 1, wherein said double-sided adhesive comprises:

a first adhesive;

a second adhesive; and, a carrier having said first adhesive fixed to a first surface thereof and said second adhesive fixed to a second surface thereof.

3. The mobile wound cover recited in claim 2, wherein said carrier comprises a polymer.

4. The mobile wound cover recited in claim 2, wherein both of said first and second adhesives comprise an acrylate adhesive.

5. The mobile wound cover recited in claim 1, wherein said protective rim may be comprised of a hydrophilic material, wherein said protective rim is arranged to create a vertical distance between said skin adhesion rim and said cover.

6. The mobile wound cover recited in claim 5, wherein said protective rim is comprised of a foam.

7. The mobile wound cover recited in claim 1, wherein said double-sided adhesive is arranged proximate an external edge of said cover thereby forming a non-adhesive section on said distal surface of said cover, said non-adhesive section defining a window.

8. The mobile wound cover recited in claim 7 further comprising a blocker releasably secured to a portion of a distal surface of said double-sided adhesive of said distal surface of said cover.

9. The mobile wound cover recited in claim 1, wherein said skin adhesion rim comprises a double-sided adhesive, said skin adhesion layer comprising a first adhesive and said rim adhesion layer comprising a second adhesive, said first and second adhesives arranged on opposite sides of a carrier layer disposed therebetween.

10. The mobile wound cover recited in claim 9 further comprising at least one blocker releasably secured to said first adhesive of said skin adhesion layer of said skin adhesion rim.

11. The mobile wound cover recited in claim 1, wherein said first aperture and second aperture are substantially colinear.

12. The mobile wound cover recited in claim 1, wherein:

said adhesive surface of said single-sided adhesive comprises one or more of acrylate adhesive or rosin ester; and, said blocker surface of said single-sided adhesive comprises a polymer.

13. A mobile wound cover, comprising:

a skin adhesion rim having a first aperture therein;

a protective rim having a cover surface and a second aperture therein, said second aperture being substantially colinear with said first aperture; and, a cover having a proximal surface configured to face away from a wound in use and an opposite distal surface, said cover comprising:

a flexible film;

a first adhesive disposed on said distal surface, said first adhesive configured to releasably adhere to said cover surface of said protective rim to seal said second aperture; and, a second adhesive disposed on said proximal surface of said cover;

wherein said flexible film is configured to be folded such that at least a portion of said first adhesive on said distal surface releasably adheres to said second adhesive on said proximal surface, thereby allowing said cover to be temporarily secured to itself when detached from said protective rim.

14. The mobile wound cover recited in claim 13, wherein said skin adhesion rim further comprises a perforation portion having a plurality of removable sections, said perforation portion being arranged within said first aperture.

* * * * *